United States Patent [19]

Missbach

[11] Patent Number: 5,633,253

[45] Date of Patent: May 27, 1997

[54] SUBSTITUTED THIOSEMICARBAZONIC ACID ESTERS

[75] Inventor: Martin Missbach, Rheinfelden, Switzerland

[73] Assignee: Ciby-Geigy Corporation, Tarrytown, N.Y.

[21] Appl. No.: 500,988

[22] PCT Filed: Nov. 15, 1994

[86] PCT No.: PCT/EP94/03779

§ 371 Date: Jul. 25, 1995

§ 102(e) Date: Jul. 25, 1995

[87] PCT Pub. No.: WO95/14687

PCT Pub. Date: Jun. 1, 1995

[30] Foreign Application Priority Data

Nov. 25, 1993 [CH] Switzerland ............... 3523/93
Dec. 3, 1993 [CH] Switzerland ............... 3616/93

[51] Int. Cl.$^6$ .............. A61K 31/54; C07D 279/06
[52] U.S. Cl. .............. 514/228.8; 544/54; 544/55
[58] Field of Search ............... 544/54, 55; 514/228.8

[56] References Cited

FOREIGN PATENT DOCUMENTS 0508955  10/1992  European Pat. Off. .
0573391  12/1993  European Pat. Off. .

*Primary Examiner*—Richard L. Raymond
*Attorney, Agent, or Firm*—Marla J. Mathias; Karen G. Kaiser

[57] ABSTRACT

The present invention relates to novel substituted thiosemicarbazonic acid esters of formula I

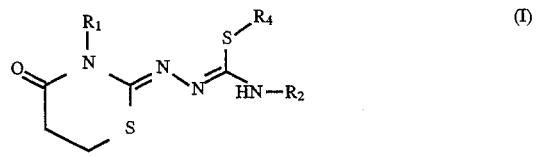

wherein $R_1$ is lower alkyl, lower alk-2-en-1-yl, lower alk-2-yn-1-yl, or aryl-lower alkyl, $R_2$ is hydrogen, lower alkyl, aryl, aryl-lower alkyl, lower alk-2-en-1-yl, lower alk-2-yn-1-yl, unsaturated or saturated heterocyclyl-lower alkyl, lower alkoxycarbonyl-lower alkyl or the group —C(=O)-$R_3$, wherein $R_3$ is lower alkyl, aryl, aryl-lower alkyl, aryl-lower alkenyl, heteroaryl (hetaryl), aryloxy, aryl-lower alkoxy or lower alk-2-en-1-yloxy, and $R_4$ is lower alkyl, lower alkoxy, lower alk-2-en-1-yl, lower alk-2-yn-1-yl, aryl-lower alkyl, aryl-lower alkenyl, or also lower alkoxycarbonyl-lower alkyl, and the salts thereof, to a process for the preparation of said compounds, to pharmaceutical compositions containing them, and to the use thereof as medicaments.

11 Claims, No Drawings

SUBSTITUTED THIOSEMICARBAZONIC ACID ESTERS

This is a 371 of PCT/EP 94/03379, filed Nov. 15, 1994.

The present invention relates to novel substituted thiosemicarbazonic acid esters of formula I

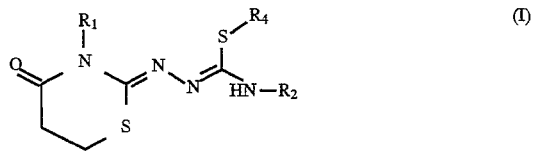

wherein $R_1$ is lower alkyl, lower alk-2-en-1-yl, lower alk-2-yn-1-yl, or aryl-lower alkyl, $R_2$ is hydrogen, lower alkyl, aryl, aryl-lower alkyl, lower alk-2-en-1-yl, lower alk-2-yn-1-yl, unsaturated or saturated heterocycly-lower alkyl, lower alkoxycarbonyl-lower alkyl or the group —C(=O)-$R_3$, wherein $R_3$ is lower alkyl, aryl, aryl-lower alkyl, aryl-lower alkenyl, heteroaryl (hetaryl), aryloxy, aryl-lower alkoxy or lower alk-2-en-1-yloxy, and $R_4$ is lower alkyl, lower alkoxy, lower alk-2-en-1-yl, lower alk-2-yn-1-yl, aryl-lower alkyl, aryl-lower alkenyl, or also lower alkoxycarbonyl-lower alkyl, and the salts thereof, to a process for the preparation of said compounds, to pharmaceutical compositions containing them, and to the use thereof as medicaments.

In this specification, radicals and compounds qualified by the term "lower" will be taken to mean those containing preferably up to and including 7, preferably up to and including 4, carbon atoms.

Lower alk-2-en-1-yl is typically $C_3$-$C_5$alk-2-en-1-yl, preferably allyl or methallyl.

Lower alk-2-yn-1-yl is typically $C_3$-$C_5$-alk-2-yn-1-yl, preferably prop-2-yn-1-yl or also but-2-yn-1-yl.

Lower alkyl is $C_1$-$C_4$alkyl, typically methyl, ethyl, propyl or butyl.

Lower alkoxy is is typically n-propoxy, isopropoxy, n-butoxy or tert-butoxy, preferably ethoxy and, most preferably, methoxy.

Aryl by itself and as moiety of composite radicals such as aryl-lower alkyl is typically phenyl or naphthyl, for example 1- or 2-naphthyl, or substituted phenyl or naphthyl, typically phenyl or naphthyl which are substituted by lower alkyl, hydroxy-lower alkyl, halo-lower alkyl, hydroxy, lower alkoxy, lower alkanoyloxy, halogen, cyano and/or nitro. Aryl is preferably unsubstituted phenyl or phenyl which is substituted as indicated above, and is most preferably phenyl.

Aryl-lower alkyl is preferably phenyl-lower alkyl and, most preferably, benzyl.

Lower alkoxycarbonyl-lower alkyl will typically be methoxy- or ethoxycarbonylmethyl or also methoxy- or ethoxycarbonylethyl.

Lower alkanoyloxy is typically propionyloxy or pivaloyloxy, and is preferably acetoxy.

Hydroxy-lower alkyl is 2- or 3-hydroxy-lower alkyl such as 2-hydroxypropyl, 3-hydroxypropyl or 3-hydroxy-2-methylpropyl.

Halogen will be taken to mean halogen having an atomic number of up to and including 35, typically chloro or fluoro, and also bromo.

Halogen-lower alkyl will typically be 2- or 3-halo-lower alkyl such as 2-halopropyl, 3-halopropyl or 3-halo-2-methylpropyl.

Unsaturated heterocyclyl-lower alkyl is typically heteroaryl-lower alkyl (hetaryl-lower alkyl).

Hetaryl in composite radicals such as hetaryl-lower alkyl is preferably a monocyclic and also bicyclic or polycyclic heterocyclic radical having aromaticity. Bicyclic and polycyclic heteroaryl may be comprised of a plurality of heterocyclic rings or, preferably, consist of one heterocycle and one or more than one, conveniently one or two and preferably one, fused carbocyclic ring, preferably a benzene ring. Each individual ring typically contains 3, 5, 6 or 7 and, preferably, 5 or 6 ring members. Hetaryl is preferably an azacyclic, thiacyclic, oxacyclic, thiazacyclic, thiadiazacyclic, oxazacyclic, diazacyclic, triazacyctic and tetrazacyclic radical.

Hetaryl is most preferably monocyclic monoazacyclic, monothiacyclic or monooxacyclic radicals such as pyrryl, e.g. 2-pyrryl or 3-pyrryl, pyridyl, e.g. 2-, 3- or 4-pyridyl, thienyl, e.g. 2- or 3-thienyl, or furyl, e.g. 2-furyl; bicyclic monoazacyclic, monooxacyclic or monothiacyclic radicals such as indolyl, e.g. 2- or 3-indolyl, quinolinyl, e.g. 2- or 4-quinolinyl, isoquinolinyl, e.g. 1-isoquinolinyl, benzofuranyl, e.g. 2- or 3-benzofuranyl, or benzothienyl, e.g. 2- or 3-benzothienyl; monocyclic diazacyclic, triazacyclic, tetrazacyclic, oxazacyclic, thiazacyclic or thiadiazacyclic radicals such as imidazolyl, e.g. 2-imidazolyl, pyrimidinyl, e.g. 2- or 4-pyrimidinyl, triazolyl, e.g. 1,2,4-triazol-3-yl, tetrazolyl, e.g. 1- or 5-tetrazolyl, oxazolyl, e.g. 2-oxazolyl, isoxazolyl, e.g. 3- or 4-isoxazolyl, thiazolyl, e.g. 2-thiazolyl, isothiazolyl, e.g. 3- or 4-isothiazolyl or 1,2,4- or 1,3,4-thiadiazolyl, e.g. 1,2,4-thiadiazol-3-yl or 1,3,4-thiadiazol-2-yl; or bicyclic diazacyclic, oxazacyclic or thiazacyclic radicals such as benzimidazolyl, e.g. benzimidazolyl, benzoxazolyl, e.g. 2-benzoxazolyl, or benzthiazolyl, e.g. 2-benzthiazolyl.

Hetaryl radicals are unsubstituted or they carry substituents. Suitable substituents at the ring carbon atoms are typically those cited above in connection with the aryl radicals and, additionally, oxo (=O). Ring nitrogen atoms may be substituted by lower alkyl, aryl-lower alkyl, lower alkanoyl, benzoyl, carboxy, lower alkoxycarbonyl, hydroxy, lower alkoxy, lower alkanoyloxy or oxido (—Ō!)

Hetaryl is most preferably pyridyl, thienyl, pyrryl or furyl.

Hetaryl-lower alkyl is most preferably pyridylmethyl, thienylmethyl, pyrrylmethyl or furylmethyl.

Saturated heterocyclyl-lower alkyl contains a 5- or 6-membered saturated heterocyclic ring which carries a nitrogen or oxygen atom and is preferably an azacyclic or oxacyclic radical which may be substituted or unsubstituted.

A saturated 6-membered heterocyclic ring may contain a nitrogen atom in addition to an oxygen atom.

A saturated 5- or 6-membered heterocyclic radical is conveniently pyrrolidinyl, piperidino, piperidyl, tetrahydrofuranyl or tetrahydropyranyl, wherein one or also more than one hydrogen atom may be replaced by one or more than one substituent, typically by lower alkyl.

A saturated 6-membered heterocyclic radical which also contains a nitrogen atom in addition to an oxygen atom is typically morpholino or also morpholinyl.

Saturated heterocyclyl-lower alkyl is most preferably pyrrolidinylmethyl, tetrahydrofuranylmethyl or also tetrahydropyranylmethyl.

Pharmaceutically acceptable acid addition salts of compounds of formula I are typically their pharmaceutically acceptable salts with suitable mineral acids such as hydrohalic acids, sulfuric acid or phosphoric acid, including hydrochlorides, hydrobromides, sulfates, hydrogensulfates or phosphates, salts with suitable aliphatic or aromatic sulfonic acids or N-substituted sulfamic acids, including methanesulfonates, benzenesulfonates, p-tosylates or N-cyclohexylsulfamates (cyclamates), or salts with strong organic carboxylic acids such as lower alkanecarboxylic acids or unsaturated or hydroxylated aliphatic dicarboxylic acids, including acetates, oxalates, malonates, maleates, fumarates, tartrates or citrates. Salts of compounds of formula I are typically the pharmaceutically acceptable salts thereof with suitable mineral acids such as hydrohalic acids, sulfuric acid or phosphoric acid, including hydrochlorides, hydrobromides, sulfates, hydrogensulfates or phosphates, salts with suitable aliphatic or aromatic sulfonic acids or N-substituted sulfamic acids, including methansulfonates, benzenesulfonates, p-tosylates or N-cyclohexylsulfamates (cyclamates).

The compounds of formula I and their pharmaceutically acceptable salts have valuable pharmacological properties. In particular, they have pronounced antiarthritic properties. These properties can be demonstrated in vivo in the adjuvans arthritis model in rats in accordance with the assay of I. Wiesenberg et al. Clin. Exp. Immunol. 78, 245 (1989) in the dosage range from about 0.1 to about 10.0 mg/kg p.o. or i.p., preferably from about 0.1 to about 3.0 mg/kg p.o. or i.p.

The compounds of formula I and their pharmaceutically acceptable salts can therefore be used for treating diseases of rheumatoid genesis. Such diseases include in particular rheumatoid arthritis, juvenile arthritis, ankylosing spondylitis and other seronegative spondylarthfides, e.g. spondylarthritides in ulcerative colitis and Crohn's disease, and also reactive arthritides, collagen diseases such as lupus erythematosus, degenerative rheumatic diseases, extraarticular rheumatic and pararheumatic diseases such as gout and osteoporosis.

The invention relates in particular to compounds of formula I, wherein $R_1$ is $C_1$–$C_4$alkyl, $C_3$–$C_5$alk-2-en-1-yl, $C_3$–$C_5$alk-2-yn-1-yl, or phenyl-lower alkyl, $R_2$ is hydrogen, $C_3$–$C_4$alkyl, $C_3$–$C_5$alk-2-en-1-yl, $C_3$–$C_5$alk-2-yn-1-yl, phenyl, naphthyl, phenyl-lower alkyl, pyridyl-lower alkyl, thienyl-lower alkyl, pyrryl-lower alkyl or furyl-lower alkyl, pyrrolidinyl-lower alkyl, tetrahydrofuranyl-lower alkyl or tetrahydropyranyl-lower alkyl, or $C_1$–$C_4$alkoxycarbonyl-$C_1$–$C_4$alkyl or the group —C(C=O)—$R_3$, wherein $R_3$ is $C_1$–$C_4$alkyl, phenyl, naphthyl, pyridyl, thienyl, pyrryl, furyl, phenoxy, phenyl-$C_1$–$C_4$alkoxy or $C_3$–$C_5$alk-2-en-1-yloxy, phenyl-lower alkyl or phenyl-lower alkenyl, and $R_4$ is $C_1$–$C_4$alkyl, $C_1$–$C_4$alkoxy, $C_3$–$C_5$alk-2-en-1-yl, $C_3$–$C_5$alk-2-yn-1-yl, or phenyl-CFC$_2$alkyl, and the salts, preferably the pharmaceutically acceptable salts, thereof.

More particularly, the invention relates to compounds of formula I, wherein $R_1$ is $C_1$–$C_4$alkyl, typically methyl or ethyl, preferably propyl, $C_3$–$C_5$alk-2-en-1-yl such as allyl or methallyl, $C_3$–$C_5$alk-2-yn-1-yl such as prop-2-yn-1-yl, or phenyl-lower alkyl such as benzyl or phenylethyl, and $R_2$ is hydrogen, $C_1$–$C_4$alkyl such as methyl or ethyl, $C_3$–$C_5$alk-2-en-1-yl, typically allyl or methallyl, $C_3$–$C_5$alk-2-yn-1-yl such as prop-2-yn-1-yl, phenyl, phenyl-lower alkyl such as benzyl or phenethyl, pyridyl-lower alkyl, thienyl-lower alkyl, pyrryl-lower alkyl or furyl-lower alkyl, pyrrolidinyl-lower alkyl, tetrahydrofuranyl-lower alkyl or tetrahydropyranyl-lower alkyl, for example pyridylmethyl, thienylmethyl, pyrrylmethyl, or furylmethyl, pyrrolidinylmethyl, tetrahydrofuranylmethyl or tetrahydropyranylmethyl, $C_1$–$C_4$alkoxycarbonyl-$C_1$–$C_4$alkyl such as methoxy- or ethoxycarbonylmethyl or methoxy- or ethoxycarbonylethyl or the group —(=O)—$R_3$, wherein $R_3$ is $C_1$–$C_4$alkyl such as methyl, phenyl, pyridyl, thienyl, phenoxy, benzoxy, $C_3$–$C_5$alk-2-en-1-yloxy such as allyloxy or methallyloxy or also benzyl or phenylallyl, and $R_4$ is $C_1$–$C_4$alkyl such as methyl or ethyl, $C_1$–$C_2$alkoxy such as methoxy or ethoxy, $C_3$–$C_5$alk-2-en-1-yl, e.g. allyl, methallyl or dimethylallyl, $C_3$–$C_5$-alkyl-2-yn-1-yl such as prop-2-yn-1-yl, or phenyl-$C_1$–$C_2$alkyl such as benzyl, and the salts, preferably the pharmaceutically acceptable salts, thereof.

The invention relates very especially to compounds of formula I, wherein $R_1$ is propyl, allyl, methallyl, prop-2-yn-1-yl or benzyl, and $R_2$ is hydrogen, methyl, allyl, prop-2-yn-1-yl, phenyl, benzyl, pyridylmethyl, thienylmethyl, pyrrylmethyl or furylmethyl, pyrrolidinylmethyl, tetrahydrofuranylmethyl or tetrahydropyranylmethyl or the group —C(=O)—$R_3$, wherein $R_3$ is methyl phenyl, phenoxy, benzoxy, allyloxy, benzyl or phenylallyl, and $R_4$ is allyl, dimethylallyl, prop-2-yn-1-yl or benzyl, and the salts, preferably the pharmaceutically acceptable salts, thereof.

The invention relates specifically to the compounds of formula I and the salts, preferably the pharmaceutically acceptable salts, thereof, named in the Examples.

The compounds of formula I can be prepared in a manner known per se by reacting a compound of formula II

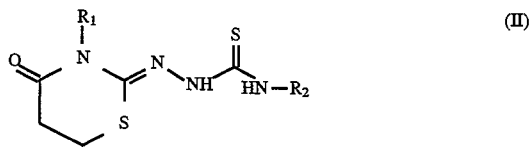

wherein $R_1$ and $R_2$ are as defined above, with a compound of formula III

wherein X is a nucleofugic leaving group.

The radical X in a compound of formula III is preferably halogen, e.g. chloro, bromo or iodo, and also e.g. sulfonyloxy which is substituted by aliphatic or aromatic groups, e.g. methylsulfonyloxy (mesilate) or 4-methylphenylsulfonyloxy (rosylate). As further leaving group, X may also be the trifluoracetate group in a compound $R_4$-X of formula III.

The condensation of a compound of formula II with a compound of formula III is carried out in the presence of a basic condensing agent, conveniently a tertiary organic base such as a tri-lower alkylamine, for example triethylamine, of a Hünig base or an organic nitrogen base such as pyridine or quinoline, in the temperature range from 25° to 120° C., conveniently at the boiling temperature of the solvent.

Suitable solvents are protic and aprotic solvents, typically aliphatic halogenated hydrocarbons such as dichloromethane, preferably methylene chloride, or aliphatic or cycloaliphatic ethers such as tetrahydrofuran or dioxane. Further suitable solvents are toluene and also ethanol.

In some cases a salt such as sodium or potassium iodide and/or a catalytic amount of dimethylaminopyridine may be added as reaction catalyst.

Starting compounds of formula II are novel and may typically be prepared by reacting a compound of formula IV

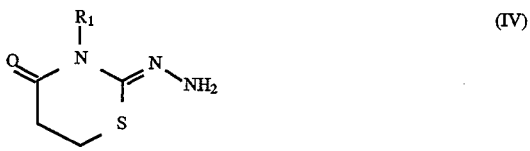

wherein $R_1$ is as defined above, with an isothiocyanate of formula V $r_2$—NCS (V)

wherein $R_2$ is as defined above.

The reaction of the hydrazone of general formula IV with an isothiocyanate of general formula V is preferably carried out in an inert solvent, conveniently in a lower alkanol such as methanol, ethanol, propanol or isopropanol, an ethereal solvent such as diethyl ether, dibutyl ether, tetrahydrofuran or dioxane, a hydrocarbon such as benzene, toluene or hexane, or a halogenated hydrocarbon such as chloroform, at room temperature or at moderately elevated temperature up to c. 100° C. or the boiling temperature of the solvent employed. Depending on the reaction temperature and the reactivity of the starting materials, the reaction time is from about half an hour to 24 hours.

Starting materials of general formula IV are also novel and can be obtained from compounds of general formula VI

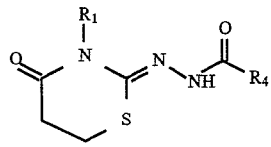
(VI)

wherein $R_1$ is as defined above and $R_4$ is a lower alkyl or aryl-lower alkyl radical, preferably methyl or benzyl, by treatment with a mineral acid, preferably hydrochloric acid.

The reaction is carried out in an anhydrous inert solvent as already noted above in connection with the reaction of compounds of formula IV with compounds of formula V, preferably in an anhydrous lower alkanol, conveniently in an anhydrous mixture of methanol and ethanol at room temperature, to give a salt, e.g. the hydrochloride, of a compound of general formula IV, which salt can be convened into the free hydrazinc by addition of a base, conveniently a solution of an alkali metal carbonate or alkaline earth metal carbonate, preferably a solution of sodium carbonate.

Compounds of general formula VI can in turn be obtained by alkylating a compound of general formula VII

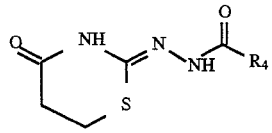
(VII)

wherein $R_4$ is as defined for formula V, with the corresponding halide of formula VIII $R_1$—X (VIII)

wherein $R_4$ is as defined for formula I, and X is a halogen atom, preferably a bromine atom.

The alkylation is carried out in an inert solvent, preferably dimethyl formamide (DMF), in the presence of a strong base, conveniently potassium tert-butylate, sodium hydride, sodium amide or also lithium diisopropylamide (LDA), to give a mixture of the N-alkylamide of general formula VI and the O-alkylated imino ether of general formula IX.

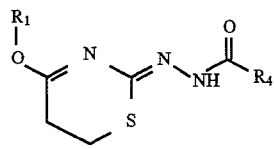
(IX)

wherein $R_1$ and $R_4$ are as defined for formula VI, in a specific ratio. The separation of the resultant compound of general formula VI from the compound of general formula IX can be effected by fractional crystallization and/or by chromatography.

Compounds of general formula VI can in turn be prepared by cyclizing the known compounds of general formula X

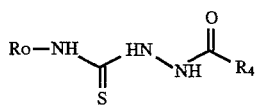
(X)

wherein $R_o$ is an acryloyl group (vinylcarbonyl group) or a radical that is convertible into an acryloyl group, e.g. 3-chloropropionyl, and $R_4$ is as defined for formula VI.

The cyclisation is carried out by gentle heating in an inert solvent as already noted above in connection with the reaction of a compound of formula IV with a compound of general formula V, preferably in a lower alkanol such as ethanol or also in acetonitrile.

The isothiocyanates of formula V can usually be prepared from the corresponding amines of formula XI $R_2$—$NH_2$ (XI)

wherein $R_2$ is as defined above, by treatment with thiophosgene.

Resultant salts can be converted in a manner known per se into other salts, acid addition salts conveniently by treatment with a suitable metal salt, typically a sodium, barium or silver salt, of another acid in a suitable solvent in which a resultant inorganic salt is insoluble and is thus eliminated from the equilibrium of reaction, and salts of bases by generating the free acid and repeated salt-formation.

The compounds of formula I, including theft salts, may also be obtained in the form of hydrates or include the solvent used for crystallisation.

Because of the close relationship between the novel compounds in the free form and in the form of their salts, the references made throughout this specification to the free compounds and their salts will also apply by analogy to the corresponding salts and free compounds.

Racemates can also be separated by known methods into the optical antipodes, conveniently by recrystallisation from an optically active solvent, with the aid of microorganisms or by reacting the mixture of diastereoisomers or racemate with an optically active compound, e.g. depending on the acid, basic or functionally modifiable groups present in the compound of formula I, with an optically active acid, base or an optically active alcohol, into mixtures of diastereoisomeric salts or functional derivatives such as esters, separating said mixtures into the diastereoisomers from which each desired enantiomer can be set free in the customary manner. Bases, acids or alcohols suitable for the purpose are typically optically active alkaloid bases such as strychine, cinchonine or brucine, or D- or L-(1-phenyl)ethylamine, 3-pipecoline, ephedrine, amphetamine or similar bases which are obtainable by synthesis, optically active carboxylic or sulfonic acids such as quinic acid or D- or L-tartaric acid, D- or L-di-o-toluyltartaric acid, D- or L-malic acid, D- or L-mandelic acid or D- or L-camphorsulfonic acid, or optically active alcohols such as borneol or D- or L-(1-phenyl)ethanol.

The invention relates also to those embodiments of the process in which a compound obtainable as intermediate in any stage of the process is used as starting material and the remaining steps are carried out, or a starting material is used in the form of a salt or, preferably, is formed under the reaction conditions.

The invention also relates to the novel starting materials which have been specially developed for the preparation of the novel compounds, especially those which result in the compounds of formula I described at the beginning as being especially preferred, to processes for their preparation and to the use thereof as intermediates.

The pharmaceutical compositions of this invention which contain the novel compound, or a pharmaceutically acceptable salt thereof, are those for enteral, e.g. oral, and also rectal and parenteral administration to warm-blooded animals, and they contain the pharmacologically active compound alone or together with a pharmaceutically acceptable carrier. The daily dose will depend on the age, sex and individual condition of the patient as well as on the mode of administration.

The novel pharmaceutical compositions contain from about 10 to 80%, preferably from about 20 to 60%, of the active compound. Pharmaceutical compositions for enteral or parenteral administration are typically those in dosage unit forms such as dragées, tablets, capsules or suppositories, and also ampoules. These dosage forms are prepared in a manner known per se, typically by conventional mixing, granulating, confectioning, dissolving or lyophilising methods. Pharmaceutical compositions for oral administration can typically be prepared by combining the the active compound with solid carriers, granulating the mixture so obtained and, if desired or necessary, processing the mixture or granulate, after addition of suitable excipients, to tablets or dragée cores.

Suitable carriers are especially fillers such as sugars, conveniently lactose, saccharose, mannitol or sorbitol, cellulose preparations and/or calcium phosphates, typically tricalcium phosphate or calcium hydrogen phosphate, and also binders such as starch pastes, conveniently using maize, corn, rice or potato starch, gelatin, tragacanth, methyl cellulose and/or polyvinyl pyrrolidone, and/or, if desired, disintegrators such as the above-mentioned starches, also carboxymethyl starch, crosslinked polyvinylpyrrolidone, agar, alginic acid or a salt thereof such as sodium alginate. Excipients are in particular glidants, flow control agents and lubricants, conveniently silica, talcum, stearic acid or salts thereof, typically magnesium stearate or calcium stearate, and/or polyethylene glycol. Dragée cores can be provided with suitable non-enteric or enteric coatings, typically using concentrated sugar solutions which may contain gum arabic, talcum, polyvinylpyrrolidone, polyethylene glycol and/or titanium dioxide, shellac solutions in suitable organic solvents or mixtures of solvents or, for the preparation of enteric coatings, solutions of suitable cellulose preparations such as acetyl cellulose phthalate or hydroxypropylmethyl cellulose phthalate. Dyes or pigments can be added to the tablets or dragée coatings, conveniently to identify or indicate different doses of active compound.

Further pharmaceutical compositions for oral administration are dry-filled capsules made of gelatin and also soft-sealed capsules consisting of gelatin and a plasticiser such as glycerol or sorbitol. The dry-filled capsules can contain the active ingredient in the form of granules, conveniently in admixture with fillers such as lactose, binders such as starches, and/or glidants such as talcum or magnesium stearate, and with or without stabilisers. In soft capsules, the active ingredient is preferably dissolved or suspended in a suitable liquid, typically a fatty oil, paraffin oil or a liquid polyethylene glycol, to which a stabiliser can also be added.

Suitable pharmaceutical compositions for rectal administration are typically suppositories, which consist of a combination of the active compound with a suppository base. Examples of suitable suppository bases are natural or synthetic triglycerides, paraffin hydrocarbons, polyethylene glycols and higher alkanols. It is also possible to use gelatin capsules for rectal administration that contain a combination of the active compound with a base substance. Suitable base substances are typically liquid triglycerides, polyethylene glycol or paraffin hydrocarbons.

Most suitable for parenteral administration are aqueous solutions of an active compound in water-soluble form, for example of a water-soluble salt, and also suspensions of the active compound, conveniently oily injection suspensions using suitable lipophilic solvents or vehicles such as fatty oils, typically sesame oil, or synthetic fatty acid esters such as ethyl oleate or triglycerides, or aqueous injection suspensions which may contain viscosity increasing substances, conveniently sodium carboxymethyl cellulose, sorbitol and/or dextran, and also with or without stabilisers.

The invention also relates to the use of the compounds of formula I, preferably in the form of pharmaceutical compositions. The dosage of the active compound will depend on the species of the warm-blooded animal, on the age and individual condition of the patient, and also on the mode of administration. The contemplated daily dosage for oral administration to a patient of approximately 75 kg body weight will normally be from about 5 mg to 1000 mg, preferably from about 10 mg to 200 mg. This dose can be administered in a single dose or in several, typically from 2 to 4, individual doses.

Pharmaceutical compositions in dosage unit form thus contain from about 5 mg to 250 mg, preferably from about 10 mg to 50 mg, of active compound.

The invention is illustrated by the following Examples. Pressures are given in mbar.

Example 1: 1 g of 1-(3-allyl-4-oxo-[1,3]thiazinan-2-ylidene)-4-methylthiosemicarbazone and 0.6 ml of methyl iodide are stirred in 15 ml of methylene chloride in the presence of 1.4 ml of triethylamine and a catalytic amount of dimethylaminopyridine for 5 hours at room temperature. Then a further 0.3 ml of methyl iodide and 0.7 ml of triethylamine are added and stirring is continued for another 12 hours at room temperature. The mixture is washed twice with water, dried over $MgSO_4$ and concentrated. The product is crystallised from ethanol at 0° C., collected by filtration, washed with petroleum ether and dried under vacuum, giving the solid 1-(3-allyl-4-oxo-[1,3]thiazinan-2-ylidene)-4-methyl-thiosemicarbazonic acid methyl ester; m.p. 112–114° C.

1H-NMR: 2.45 (s, 3H), 2.9 (m, 7H), 3.75 (d, 2H), 4.65 (d, 2H), 5.1–5.25 (m, 2H), 5.75–5.95 (m, 2H).

Example 2: With stirring, 0.6 g of 1-(3-allyl-4-oxo-[1,3] thiazinan-2-ylidene)-4-methylthiocarbazone and 0.4 g of allyl bromide are refluxed for 4 hours in 20 ml of methylene chloride with a catalytic amount of dimethylaminopyridine. Then a further 0.4 g of allyl bromide are added and the mixture is refluxed for another 8 hours. After cooling to room temperature, the reaction mixture is washed twice with a saturated solution of $Na-HCO_3$, dried over $MgSO_4$ and concentrated. The product is crystallised from ether/ pentoleum ether at 0° C., collected by filtration, washed with petroleum ether and dried under vacuum, giving the solid 1-(3-allyl-4-oxo-[1,3]thiazinan-2-ylidene)-4-methylthiosemicarbazonic acid allyl ester; m.p. 70°–74° C.

1H-NMR: 2.9 (m, 7H), 3.75 (d, 2H), 4.65 (d, 2H), 5.1–5.4 (m, 4H), 5.7 (m, 1), 5.8–6.1 (m, 2H).

Example 3: With stirring, 0.5 g of 1-(3-allyl-4-oxo-[1,3]thiazinan-2-ylidene)-4-methylthiosemicarbazone and 0.35 g of benzyl bromide are refluxed for 4 hours in 20 ml of tetrahydrofuran in the presence of 0.3 ml of triethylamine and a catalytic amount of dimethylaminopyridine. After cooling to room temperature, the solvent is stripped off on a rotary evaporator and the residue is taken up in methylene chloride. The mixture is washed twice with water, dried over MgSO₄ and concentrated. The residue is chromatographed on silica gel with methylene chloride as eluant and the product is dissolved in acetone. After addition of HCl in ethanol, the product is crystallised by addition of ether. The crystalline product is collected by filtration, washed with ether and dried under vacuum, giving the hydrochloride of 1-(3-allyl-4-oxo-[1,3]thiazinan-2-ylidene)-4-methylthiosemicarbazonic acid benzyl ester, m.p. 124°–125° C.

1H-NMR: 2.9 (m, 7H), 4.35 (s, 2H), 4.65 (d, 2H), 5.1–5.25 (m, 2H), 5.75–5.95 (m, 2H), 7.2–7.5 (m, 5H).

Example 4: Tablets each containing 10 mg of active ingredient may be prepared as follows:

| Composition (10 000 tablets) | |
|---|---|
| active ingredient | 100.0 g |
| lactose | 450.0 g |
| potato starch | 350.0 g |
| gelatin | 10.0 g |
| talcum | 60.0 g |
| magnesium stearate | 10.0 g |
| silica (highly dispersed) | 20.0 g |
| ethanol | q.s. |

The active ingredient is mixed with the lactose and 292 g of potato starch. The mixture is moistened with an ethanolic solution of gelatin and granulated through a sieve. The granulate is dried and the remainder of the potato starch, the talcum, the magnesium stearate and the silica are added and the mixture is compressed to 100.0 mg tablets each containing 10.0 mg of active ingredient. If desired, the tablets can be provided with a breaking notch for finer adjustment of the dose.

Example 5: Hard gelatin capsules containing 20 mg of active ingredient may be prepared as follows:

| Composition (for 1000 capsules) | |
|---|---|
| active ingredient | 20.0 g |
| lactose | 240.0 g |
| microcrystalline cellulose | 30.0 g |
| sodium lauryl sulfate | 2.0 g |
| magnesium stearate | 8.0 g |

The sodium lauryl sulfate is sieved through a sieve having a mesh size of 0.2 mm and added to the lyophilised active ingredient and both components are thoroughly mixed. First the lactose is passed through a sieve having a mesh size of 0.6 mm and then the microcrystalline cellulose is passed through a sieve having a mesh size of 0.9 mm. The ingredients are then thoroughly mixed again for 10 minutes. Finally, the magnesium stearate is passed through a sieve having a mesh size of 0.8 mm. After mixing for 3 minutes, size 0 hard gelatin capsules are each filled with 300 mg of the formulation so obtained.

Example 6: Hard gelatin capsules containing 100 mg of active ingredient may be prepared as follows:

| Composition (for 1000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is sieved through a sieve having a mesh size of 0.2 mm and added to the lyophilised active ingredient and both components are thoroughly mixed. First the lactose is passed through a sieve having a mesh size of 0.6 mm and then the microcrystalline cellulose is passed through a sieve having a mesh size of 0.9 mm. The ingredients are then thoroughly mixed again for 10 minutes. Finally, the magnesium stearate is passed through a sieve having a mesh size of 0.8 mm. After mixing for 3 minutes, size 0 hard gelatin capsules are each filled with 390 mg of the formulation so obtained.

Example 7: Film-coated tablets each containing 50 mg of active ingredient may be prepared as follows:

| Composition (for 1000 film-coated tablets) | |
|---|---|
| active ingredient | 50.0 g |
| lactose | 100.0 g |
| corn starch | 70.0 g |
| talcum | 10.0 g |
| calcium stearate | 2.0 g |
| hydroxypropyl methyl cellulose | 2.36 g |
| shellac | 0.64 g |
| water | q.s. |
| methylene chloride | q.s. |

The active ingredient, the lactose and 40 g of corn starch are mixed and moistened with a paste prepared from 15 g of corn starch and water (with heating), and the mixture is granulated. The granulate is dried, the remainder of the corn starch, the talcum and the calcium stearate are added and mixed with the granulate. The mixture is compressed to 240 mg tablets which are coated with a solution of hydroxypropyl methyl cellulose and shellac in methylene chloride. Final weight of the tablets: 283 mg.

Example 8: A 0.2% injection or infusion solution of the active ingredient may be prepared as follows:

| Composition (for 1000 ampoules) | |
|---|---|
| active ingredient | 5.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and the solution is filtered through a microfilter. The buffer solution is added, followed by the addition of water to make up 2500 ml. To prepare dosage unit forms, 1.0 or 2.5 ml of the solution are filled into glass ampoules each containing 2.0 or 5.0 mg of active ingredient.

Example 9: 1% ointment (O/W emulsion), containing an active ingredient, of the following composition:

| | |
|---|---|
| active ingredient | 1.0 g |
| cetyl alcohol | 3.0 g |
| glycerol | 6.0 g |
| methyl parabene | 0.18 g |
| propyl parabene | 0.05 g |
| Arlacel 60 | 0.6 g |
| Tween 60 | 4.4 g |
| stearic acid | 9.0 g |
| isopropyl palmitate | 2.0 g |
| paraffin oil, viscous | 10.0 g |
| demin. water q.s. ad | 100.0 g |

Example 10:1% gel, containing an active ingredient, of the following composition:

| | |
|---|---|
| active ingredient | 1.0 g |
| Carbopol 934 P | 1.0 g |
| glycerol | 3.0 g |
| isopropanol | 25.0 g |
| Softigen® 767 | 0.2 g |
| demin. water q.s. ad | 100.0 g. |

What is claimed is:

1. A compound of formula I

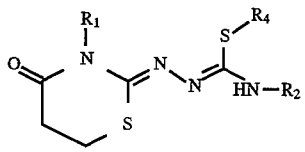

wherein $R_1$ is lower alkyl, lower alk-2-en-1-yl, lower alk-2-yn-1-yl, or aryl-lower alkyl, $R_2$ is hydrogen, lower alkyl, aryl, aryl-lower alkyl, lower alk-2-en-1-yl, lower alk-2-yn-1-yl, unsaturated or saturated heterocycly-lower alkyl, lower alkoxycarbonyl-lower alkyl or the group —C(=O)-$R_3$, wherein $R_3$ is lower alkyl, aryl, aryl-lower alkyl, aryl-lower alkenyl, heteroaryl (hetaryl), aryloxy, aryl-lower alkoxy or lower alk-2-en-1-yloxy, and $R_4$ is lower alkyl, lower alkoxy, lower alk-2-en-1-yl, lower alk-2-yn-1-yl, aryl-lower alkyl, aryl-lower alkenyl, or also lower alkoxycarbonyl-lower alkyl, or a salt thereof.

2. A compound of formula I according to claim 1, wherein $R_1$ is $C_1$–$C_4$alkyl, $C_3$–$C_5$alk-2-en-1-yl, $C_3$–$C_5$alk-2-yn-1-yl, or phenyl-lower alkyl, $R_2$ is hydrogen, $C_1$–$C_4$alkyl, $C_3$–$C_5$alk-2-en-1-yl, $C_3$–$C_5$alk-2-yn-1-yl, phenyl, naphthyl, phenyl-lower alkyl, pyridyl-lower alkyl, thienyl-lower alkyl, pyrryl-lower alkyl or furyl-lower alkyl, pyrrolidinyl-lower alkyl, tetrahydrofuranyl-lower alkyl or tetrahydropyranyl-lower alkyl, or $C_1$–$C_4$alkoxycarbonyl-$C_1$–$C_4$alkyl or the group —C(C=O)-$R_3$, wherein $R_3$ is $C_1$–$C_4$alkyl, phenyl, naphthyl, pyridyl, thienyl, pyrryl, furyl, phenoxy, phenyl-$C_1$–$C_4$alkoxy or $C_3$–$C_5$alk-2-en-1-yloxy, phenyl-lower alkyl or phenyl-lower alkenyl, and $R_4$ is $C_1$–$C_4$alkyl, CrC$_4$alkoxy, $C_3$–$C_5$alk-2-en-1-yl, $C_3$–$C_5$alk-2-yn-1-yl, or phenyl-$C_1$–$C_2$alkyl, or a pharmaceutically acceptable salt thereof.

3. A compound of formula I according to claim 1, wherein $R_1$ is $C_1$–$C_4$alkyl, $C_3$–$C_5$alk-2-en-1-yl, $C_3$–$C_5$alk-2-yn-1-yl, or phenyl-lower alkyl, and $R_2$ is hydrogen, $C_1$–$C_4$alkyl, $C_3$–$C_5$alk-2-en-1-yl, $C_3$-$C_5$alk-2-yn-1-yl, phenyl, phenyl-lower alkyl, pyridyl-lower alkyl, thienyl-lower alkyl, pyrryl-lower alkyl, furyl-lower alkyl, pyrrolidinyl-lower alkyl, tetrahydrofuranyl-lower alkyl, tetrahydropyranyl-lower alkyl, $C_1$–$C_4$alkoxycarbonyl-$C_1$–$C_4$alkyl or the group —(=O)—$R_3$, wherein $R_3$ is $C_1$–$C_4$alkyl, phenyl, pyridyl, thienyl, phenoxy, benzoxy, $C_3$–$C_5$alk-2-en-1-yloxy, benzyl or phenylallyl, and $R_4$ is $C_1$–$C_4$alkyl, $C_1$–$C_2$alkoxy, $C_3$–$C_5$alk-2-en-1-yl, $C_3$–$C_5$alkyl-2-yn-1-yl, or phenyl-$C_1$–$C_2$alkyl, or a pharmaceutically acceptable salt thereof.

4. A compound of formula I according to claim 3, wherein $R_1$ is methyl, ethyl, propyl, allyl, methallyl, prop-2-yn-1-yl, benzyl or phenylethyl, $R_2$ is hydrogen, methyl, ethyl, allyl, methallyl, prop-2-yn-1-yl, phenyl, benzyl, phenethyl, pyridylmethyl, thienylmethyl, pyrrylmethyl, furylmethyl, pyrrolidinylmethyl, tetrahydrofuranylmethyl, tetrahydropyranylmethyl, methoxy- or ethoxycarbonylmethyl or methoxy- or ethoxycarbonylethyl, or the group —(=O)-$R_3$, wherein $R_3$ is methyl, phenyl, pyridyl, thienyl, phenoxy, benzoxy, allyl, methallyloxy, benzyl or phenylallyl, and $R_4$ is methyl, ethyl, methoxy, ethoxy, allyl, methallyl, dimethylallyl, prop-2-yn-1-yl, or benzyl, or a pharmaceutically acceptable salt thereof.

5. A compound of formula I according to claim 1, wherein $R_1$ is propyl, allyl, methallyl, prop-2-yn-1-yl or benzyl, and $R_2$ is hydrogen, methyl, allyl, methallyl, prop-2-yn-1-yl, phenyl, benzyl, pyridylmethyl, thienylmethyl, pyrrylmethyl or furylmethyl, pyrrolidinylmethyl, tetrahydrofuranylmethyl or tetrahydropyranylmethyl or the group —C(=O)—$R_3$, wherein $R_3$ is methylphenyl, phenoxy, benzoxy, allyloxy, benzyl or phenylallyl, and $R_4$ is allyl, dimethylallyl, prop-2-yn-1-yl or benzyl, or a pharmaceutically acceptable salt thereof.

6. A compound according to claim 1, said compound being 1-(3-allyl-4-oxo-[1,3]thiazinan-2-ylidene)-4-methylthiosemicarbazonic acid methyl ester or a pharmaceutically acceptable salt thereof.

7. A compound according to claim 7, said compound being 1-(3-allyl-4-oxo-thiazinan-2-ylidene)-4-methylthiosemicarbazonic acid allyl ester or a pharmaceutically acceptable salt thereof.

8. A compound according to claim 1, said compound being 1-(3-allyl-4-oxo-thiazinan-2-ylidene)-4-methylthiosemicarbazonic acid benzyl ester or a pharmaceutically acceptable salt thereof.

9. A pharmaceutical composition comprising a compound according to claim 1 and at least one customary pharmaceutical excipient.

10. A pharmaceutical composition suitable for oral or parenteral administration to mammals for the treatment of diseases of rheumatoid genesis, comprising a pharmacologically effective amount of a compound as claimed in claim 1, in conjunction with one or more pharmaceutically acceptable carriers.

11. A method of treating a disease of rheumatoid genesis to an animal in need thereof comprising administration of a pharmacologically effective amount of a compound according to claim 1 to an animal in need thereof.

* * * * *